United States Patent [19]

Tiernan et al.

[11] Patent Number: 5,346,699

[45] Date of Patent: Sep. 13, 1994

[54] METHOD FOR CONTROLLING PESTS BY A PESTICIDAL FOAM

[75] Inventors: Barbara H. Tiernan, Cupertino; Stanley M. Woogerd, San Rafael, both of Calif.

[73] Assignee: Foam Innovations, Inc., Pleasanton, Calif.

[21] Appl. No.: 63,361

[22] Filed: May 17, 1993

Related U.S. Application Data

[63] Continuation of Ser. No. 739,139, Jul. 31, 1991, abandoned, which is a continuation-in-part of Ser. No. 648,142, Apr. 11, 1991, abandoned, which is a continuation of Ser. No. 346,644, May 3, 1989, abandoned.

[51] Int. Cl.$^5$ ............................................. A01N 25/16
[52] U.S. Cl. ...................... 424/405; 424/43; 424/DIG. 11; 514/919; 514/945
[58] Field of Search ........................... 119/159, 160; 424/DIG. 11, 405

[56] References Cited

U.S. PATENT DOCUMENTS 4,487,553 12/1984 Nagata ........................... 417/171
4,809,462 3/1989 Maeda ............................. 43/124
4,822,613 4/1989 Rodero ........................... 424/405
4,889,710 12/1989 Hagarty ........................... 424/45

FOREIGN PATENT DOCUMENTS 027238 6/1988 European Pat. Off. .
WO9012502 11/1990 PCT Int'l Appl. .

Primary Examiner—Thurman K. Page
Assistant Examiner—Neil Levy
Attorney, Agent, or Firm—Fliesler, Dubb, Meyer & Lovejoy

[57] ABSTRACT

A method is set forth of controlling pests such as termites. The method comprises mixing a residual pesticide with a foaming agent, water and air to produce a temporary non-solidifying pesticidal foam having an expansion ratio, defined as the ratio of the final foam volume to the sum of the volumes of the pesticide, the foaming agent and the water, of between 20 to 1 and 5 to 1. The foam is applied at a locus whereby it contacts a surface which defines the locus, and thereafter deposits the pesticide on the surface and dissipates, so as to provide residual pesticidal action on the surface.

19 Claims, 4 Drawing Sheets

METHOD FOR CONTROLLING PESTS BY A PESTICIDAL FOAM

CROSS-REFERENCE

This application is a continuation of Ser. No. 07/739,139, filed Jul. 31, 1991, now abandoned which is a continuation-in-part of Ser. No. 07/648,142, filed Apr. 11, 1991, now abandoned, which is a continuation of Ser. No. 07/346,644, filed May 3, 1989, now abandoned.

TECHNICAL FIELD

This invention relates to a method of applying pesticides to irregular and hard to reach places such as below concrete slabs and low floors.

BACKGROUND OF THE INVENTION

Many pests are difficult to control with pesticides.

Termites, for example, must have moisture and must transport food to their subterranean colonies in order to live. Consequently, they must return to the ground around or beside a building after they have eaten part of the building. If one can cut off their entry or exit, one can substantially control them. A pesticide should therefore, preferably be applied at the areas of the building where the supporting structures touch the ground, or where the termites or other pests will enter or exit. When pesticide is applied to these areas, the pests, such as termites can be controlled; but often they cannot be controlled by spraying or by application of pesticidal liquid when the areas lie under a concrete slab or similar obstruction, for example under a wooden floor which is only a few inches off of the ground. Cavities often develop beneath slabs, where the pests, including termites, can collect. They can also go from these cavities to the bottom of the slab. If the ground is porous, liquid termiticide or repellant must not only be applied in large quantities to reach the bottom of the slab, resulting in overdosing, but it may be actually impossible to fill the cavity. Further, even in the absence of cavities, liquid interjected at intervals cannot migrate horizontally in porous or moderately porous ground in the way necessary to form the continuous barrier required to effectively prevent pest passage. The above problems have been increased due to the fact that present day termite pesticides are somewhat less effective than previous termite pesticides which, unfortunately, have been discovered to have unacceptable environmental impacts. Thus, with present day termite pesticides it is even more important that they be distributed over all of the space beneath concrete slabs and the like.

Thus, there are disadvantages with liquid pesticide and with pesticide sprays.

One method which has been tried to apply pesticides is via the generation of what is commonly referred to as a dry foam. Japanese patent publication SHO 58-43050, for example, shows the use of foams which include a termite pesticide, a foaming agent, an emulsifier and water. The foam is applied utilizing apparatus which is used to chemically extinguish fires. Such an apparatus typically forms large volumes of foam in very short periods of time and the resulting foams have an expansion ratio, defined as the ratio of foam volume to volume of solution being foamed, of 100 to 1 or greater. Further, the practical example set forth in the publication shows filling a volume approximately 1.5 feet high by 27 mats, each of which is 18 square feet in area, utilizing approximately 1.75 cubic feet of solution. The total cubic volume being filled is then $1.5 \times 27 \times 18 = 729$ cubic feet. Dividing this by 1.75 cubic feet gives an expansion ratio of 417 to 1. Japanese patent publication SHO 60-34901 has a similar disclosure and shows an expansion ratio of 150–500, preferably 200–400 liters per kilogram which is substantially the same per liter (liter per liter) as one kilogram of water occupies one liter in volume. The lowest expansion ratio shown, for a composition not of the invention, is less than 50 but is not otherwise specified. Japanese patent publication SHO 58-17161 is also of interest in this respect. The smallest expansion ratio (bubble multiplication) shown in the examples is 140 to 1.

Each of the aforementioned publications shows only the preparation of so-called dry foams and their application to relatively large crawl spaces. Dry foams do not flow well and, hence, cannot adequately conform to irregular ground shapes. Thus, if they were to be injected beneath building slabs, which is not contemplated by the publications and has not been attempted, they would not be capable of contacting the entire ground surface if that surface is irregular. Basically, they will simply hang out over small trenches, cavities and the like leaving the bottoms of such untouched. Since the crawl spaces treated by the foams of the publications are very large a sufficient amount of termiticide can apparently be deposited (but not on all surfaces as just discussed) in a single application, although, as a practical matter this seems doubtful and there has apparently not been an extensive commercial development of this technology.

Because of the large expansion ratio the methods of these publications are not applicable in the least to the depositing of pesticide via foams in relatively small spaces such as those below building slabs. Current state regulations require coverage of a specific amount of pesticide per linear foot (the regulations tend to specify linear foot as they envision depositing the pesticide only along the borders of slabs and the like or along trenches, etc. The regulations as to DURSBAN pesticide, a trademark of The Dow Chemical Company, is generally 15 grams per linear foot, as an example) and also require that the solution used to deliver this specific amount of coverage contain no more than a specified percent, generally between 0.5 and 1.5%, of the pesticide. To attain the specified coverage utilizing such a solution and utilizing expansion ratios as are set forth in the above described publications would require multiple fillings and dissipations of the foams or use of far larger concentrations of pesticide in solution than is allowable or safe. Furthermore, the purpose of the foam application in the publications is to allow the foam and the insecticide to be slowly absorbed into wood pillars and the like. This acts much like the conventional creosol soaking of such members to protect them from termite attack. Since the foams are purposefully made long lasting so as to allow them to be absorbed by the wooden members, multiple applications of such high expansion ratio (and relatively low pesticide concentration) foams to spaces beneath building slabs would be far too time and labor consuming so as to be practical.

British patent specification 1 274 442 is of interest in this area in that it shows the preparation of foams for being directly contacted with pests such as bacteria within closed containers or pipelines, apparently those associated with the food industry such as the milk and beer industries. Essentially, the containers or pipelines are filled with the foam which remains in place for a long enough time so that the pests can contact it directly and thereby be controlled. In the food industry deposition of residual pesticides would be highly undesirable since contamination of the food (or drink) would almost certainly occur. Hence, this publication is not concerned with foam deposition of pesticides, especially not of residual pesticides, or, if potentially residual pesticides are used it is important that they can be readily and thoroughly washed from any surfaces upon which they might be temporarily deposited. Thus, this publication is not directed to the deposition of pesticides onto the surfaces beneath slabs and the like to produce a residual pesticidal effect.

U.S. Pat. No. 4,822,613, issued Apr. 18, 1989 to A. Rodero discusses the preparation of highly stable pesticide containing water soluble foams which can be formed in situ utilizing a propellant, generally in a spray can type of arrangement. The patent discusses a foam which remained in place for a week. Control of pests is evidently via direct contact with the foam which may be generated in place in a drain pipe. The foam can be washed away when it has done its job by flushing with water. This patent is apparently not concerned with depositing a pesticide on a surface so as to provide residual pesticidal activity. The foams, to have the required long term stability, must be highly expanded dry foams since a wet foam would collapse more rapidly.

U.S. Pat. No. 3,692,512 shows the preparation of foams for applying chemicals to plants, soil or the like in the open utilizing a foam. The foam desirably is stable in the sense that it will stay moist on the plants surface for at least ten to fifteen minutes. This patent is in no way concerned with deposition of pesticide from a foam delivery system into confined spaces such as below building slabs or with providing a residual pesticidal effect in such places.

It would be highly desirable if a method were available for coating the irregular small spaces below building slabs in such a manner that the bottoms of the slabs as well as the relatively irregular ground surface below the slabs could have a pesticide effectively deposited on them, particularly a residual pesticide, and if all of this could be accomplished utilizing a solution having an allowable amount of pesticide dissolved in it to provide at least the minimum government required coverage of pesticide per unit area. The providing of such a method constitutes the main objective of the present invention.

DISCLOSURE OF INVENTION

In accordance with an embodiment of the invention a method is set forth of controlling pests such as termites. A residual pesticide is mixed with a foaming agent, water and air to produce a temporary non-solidifying pesticidal foam having an expansion ratio, defined as the ratio of the final foam volume to the sum of the volumes of the pesticide, the foaming agent and the water, of between 20 to 1 and 5 to 1. The foam is applied at a locus whereby it contacts a surface which defines the locus, and thereafter deposits the pesticide on the surface and dissipates, so as to provide residual pesticidal action on the surface.

In accordance with another embodiment of the invention a method is set forth of controlling pests beneath a concrete-slab-based building or concrete slabs associated with other buildings. The method comprises forming holes through the slab along its marginal edges or other areas within the slab to a locus beneath the slab. A residual pesticide is mixed with a foaming agent, water and air to produce a temporary non-solidifying pesticidal foam having an expansion ratio, defined as the ratio of the final foam volume to the sum of the volumes of the pesticide, the foaming agent and the water, of between 20 to 1 and 5 to 1. The pesticidal foam is injected through the holes so that it contacts a surface which defines the locus and thereafter deposits the pesticide on the surface and dissipates, so as to provide residual pesticidal action on the surface.

The present invention, instead of employing sprays or applications of liquid, relies on applying pesticidal foam, more specifically a wet pesticidal foam having a relatively low expansion ratio and which is designed to dissipate after a relatively short time, the wet foam being as defined herein. In order to apply the pesticidal foam under a slab, it is often necessary to inject the material beneath the slab through small openings or holes, which can be drilled through the slab. For example, openings that are 9/16" wide are typically drilled approximately every 18" along a marginal area forming the perimeter of the slab or in other areas within the slab. The foam stays within the cavity until it is filled to capacity. It flows sufficiently to fill in crevices, trenches, cavities and the like, thus providing pesticidal deposition over uneven surfaces. Foam will move over even extremely porous bases without running off, draining, or puddling in a single place. The treatment according to this invention is therefore able to be quite uniform in the amounts per square inch that can be applied, as compared to what one might think. Thus, the invention makes it possible to reach the pests, such as termites, in various locations beneath the slab, including the ground under the slab whether it is level and/or porous or not, and to reach the actual underground surface of the slab that lies above the empty cavities, though beneath the normal ground level. The result is the deposition of the pesticide, generally a residual pesticide, on the surfaces which define the cavity. Also, if desired the foam can be used in combination with treatment with liquid. For example, a liquid formulation can be sprayed in or flowed into the space beneath a slab or along its periphery to provide a high level of pesticide on the ground. Thereafter (or therebefore, if desired), the foam of the invention can be applied to provide pesticide deposition on portions of the ground which are not reached by the liquid and/or on the bottom of the slab.

Other objects and advantages of the invention will appear in the following description.

BRIEF DESCRIPTION OF THE DRAWINGS

The invention will be better understood by reference to the figures of the drawings wherein like numbers denote like parts throughout and wherein.

BEST MODE FOR CARRYING OUT INVENTION

Figure 2:
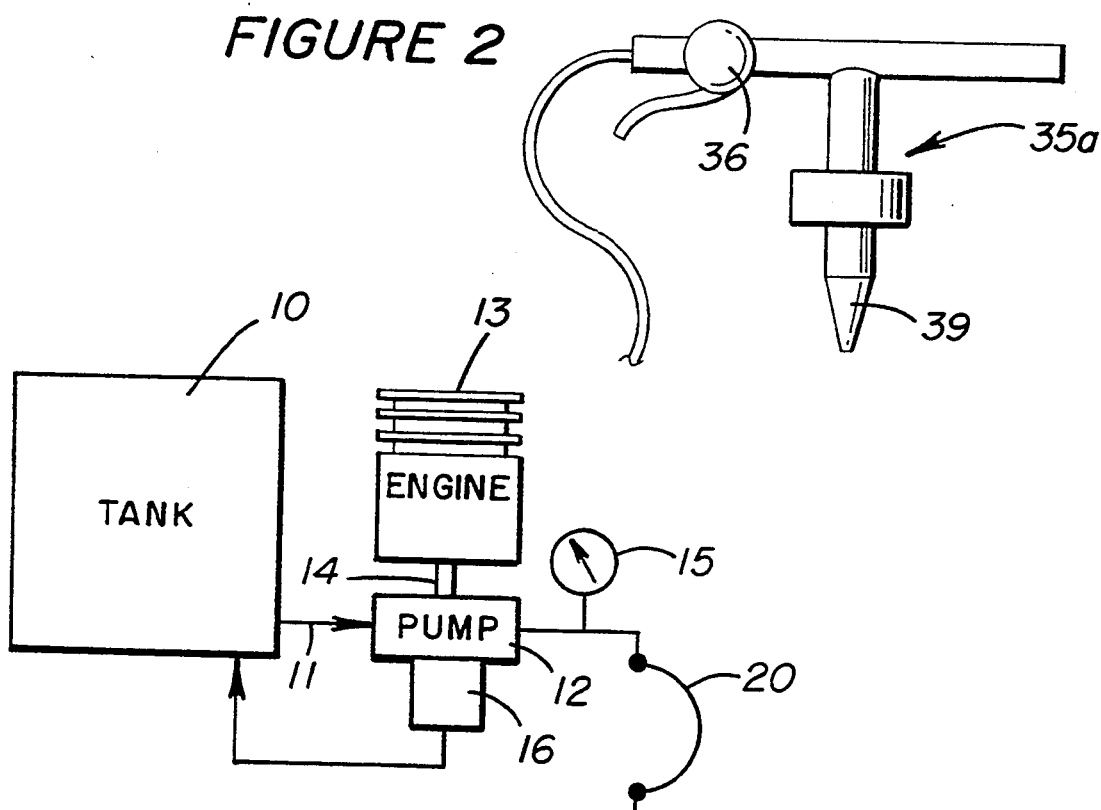
FIG. 2 is a fragmentary view in elevation of a modified form of foam applicator for use with a system like that of FIG. 1.

The first step in the method of practicing the present invention is to mix the pesticide with water, with surfactant (or "foaming agent") and with air to provide foam. The foam that is to be applied is preferably a particularly clinging wet foam that contains not only the pesticide, the foaming agent, and the water, but also sufficient air to make it an effective foam, and the foam can be drier or wetter depending on the location to which it is to be applied. Such a foam is, of course, temporary and does not solidify but instead dissipates over a period of time as the liquid settles out and the air bubbles burst.

The term pesticide as used herein includes toxicants, repellents, attractants, chemosterilants, defoliants, desiccants, disinfectants, growth regulators and phenomes. If the pests being controlled are termites or ants the pesticide will generally be a toxicant or a repellant. Mixtures of pesticides may also be applied in accordance with the invention. Thus, for example, a volatile high toxicity pesticide which dissipates quickly might be used along with a residual toxicant and/or repellant.

The pesticide is preferably chosen with reference to the particular pest which is to be attacked. The pests may be termites, ants, spiders, mites, roaches, fleas, house nesting flies, silverfish, lice, earwigs, wasps, bees, sowbugs, or crickets.

Pesticides, especially insecticides, which have been found to be suitable for application in a foam to confined spaces, include foams containing carbamates, pyrethroids, organophosphates, chlorinated hydrocarbons and various growth regulators. For example, carbamates can be combined with foaming surfactants to make foams that will be pesticidal to Lepidoptera (moths, skippers, butterflies, etc.); Orthopetra (roaches, locusts, grasshoppers, crickets, manrises, etc.); Diptera (flies, mosquitoes, gnats, midges, etc.); Coleoptera (beetles); Isoptera (termites); Hymenoptera (ants, bees, wasps, yellow jackets, hornets, etc.); Thysanura (silver fish, firebrats, etc.); Anoplura (lice, etc.); Thysanoptera (thrips, etc.); Dermaptera (earwigs, etc.); Isopoda (sow bugs, pull bugs, etc.); Diplopoda (millipedes, etc.); and Chilopoda (centipedes, etc.).

Pyrethrins can also be used to control Lepidoptera, Hemiptera, Orthoptera, Diptera, Coleoptera, Hymenoptera, Thysanura, Araneida, Acarina, Siphonaptera, and Isopoda.

Similarly, pyrethroids can be used to control Lepidoptera; Hemiptera; Orthoptera; Diptera; Homoptera (leaf hoppers, tree hoppers, cicadas, spittle bugs, etc.); Coleoptera; Hymenoptera; Araneida; Acarina; Siphonaptera (fleas, etc.); Thysanoptera; Dermaptera; Isopoda; and Chilopoda. It may also be used for controlling Isoptera, i.e., termites.

Organophosphates may be used to control Lepidoptera, Orthoptera, Diptera, Coleoptera, Hymenoptera, Thysanura, Araneida, Acarina, Siphonaptera, and Isopoda.

Foams made from chlorinated hydrocarbons and foaming agents may be used to control Isoptera (termites). Growth regulators, such as Gencor, may be used to control orthoptera.

Borates may be used to control Isoptera (termites) and Coleoptera (beetles).

It is generally preferred that the pesticide have a residual effect. Such pesticides are generally referred to in the trade as residually effective pesticides. The term residual, when applied to pesticides is defined in "Pesticides Theory and Application", George W. Ware, W. H. Freeman and Company, New York, 1983 as "Having a continued lethal effect over a period of time." and such definition is that used herein.

It should be noted that while knock down has some desirability it is of relatively little importance when the foam is used to deliver pesticide which is used to protect wooden structural parts and buildings from pests such as termites and ants. In such instances what is necessary is a residual effect. The pesticide need not be effective as a toxicant. A repellant property can be equally or more effective in attaining the desired result, so long as the pesticidal activity is residual.

All these classes of insecticides with the added foaming agents, have been tested for foaming to make a foam that is suitable for application to confined spaces. Commercial formulations of pesticides are particularly difficult to get to achieve an effective foam (generally defined as an air to liquid ratio, more properly a foam volume to contained liquid volume ratio, of greater than 5:1). This invention overcomes that difficulty as follows.

The liquid substance from which the pesticide foam is made may comprise a pesticide, a foaming agent, and water. The liquid pesticide and water may be combined with the liquid foaming agent in a suitable receptacle or tank 10, and the combined solution may be pumped into a given quantity of compressed air. The amount of compressed air and foaming agent used will vary with the pesticide and the application.

In accordance with the invention the amount of compressed air will be such as to provide a wet foam, which, for the purpose of this disclosure is defined as an effective foam having an expansion ratio of between 5 to 1 and 20 to 1, more preferably of between 6 to 1 and 15 to 1 and more preferably still of between 7 to 1 and 12 to 1. Such foams have flowability characteristics which allow them to flow into cracks, crevices, trenches, cavities and the like and are sufficiently concentrated in pesticide so as to provide reasonably high levels of a residual pesticide upon the surfaces which they contact utilizing pesticidal solutions which do not have unacceptably high levels of the pesticide.

Flowability is a measure of the rate at which a foam flows, or foam fluidity and is definable by the following test The equipment used for determining foam fluidity for purposes of this invention consists of a rigid cylindrical tank measuring 29 cm in diameter and 37 cm in length. The top surface and cylindrical wall of the tank are closed, except for a small orifice in each. The base of the tank is closed. Specifically, the top surface of the tank has a 6 cm (diameter) orifice within about 1 cm from the tank perimeter. The lower portion of the cylindrical wall has a 5 cm (diameter) orifice within about 1 cm from the base of the tank, and diametrically opposite the orifice in the top surface. The tank is oriented such that its vertical axis is at a 45° angle with the horizontal and the 5 cm orifice projects downwardly.

In use, the 5 cm orifice is sealed and the tank is filled through the 6 cm orifice with the foam to be tested. Upon complete filling, the seal is removed immediately from the 5 cm orifice. The time required to drain the tank is a measure of the flowability of the foam. (Since burrs or other rough features in the 5 cm orifice can increase the friction experienced by the draining foam and therefore adversely impact the time for draining, the 5 cm orifice should be smooth-walled.)

Acceptable flowability results when the time is less than 30 seconds. Foams with an air-to-solution ratio above 20:1 have a rigidity which causes them to lack fluidity, i.e., require more than 30 seconds to drain completely from the tank.

Also, while foams with expansion ratios between 5 to 1 and 20 to 1 have reasonable lasting properties, by which is meant they last long enough to expand into a desired space and deposit their pesticide on the surfaces that they contact, they dissipate within a reasonable time, as well, for example in 5 to 20 minutes, preferably in 5 to 10 minutes, whereby if more pesticide is necessary than can be deposited in a single filling operation using pesticidal solution containing an allowable concentration of pesticide, such can be accomplished by retreating the cavity with an additional aliquot of foam.

The solution, mixed with air, is pushed through an apparatus, mixing Chamber 31, which "works" the combination into a foam, as by moving it past various surfaces, thereby refining it into small dense bubbles and increasing the uniformity and durability of the bubbles or foam particles.

Once the foam has been properly formed and worked, it is ejected through a probe into a confined space or is spread with a tool designed to spread the foam to a desired height and width, as called for by the applications. The length and type of tool vary with the job.

Figure 1:
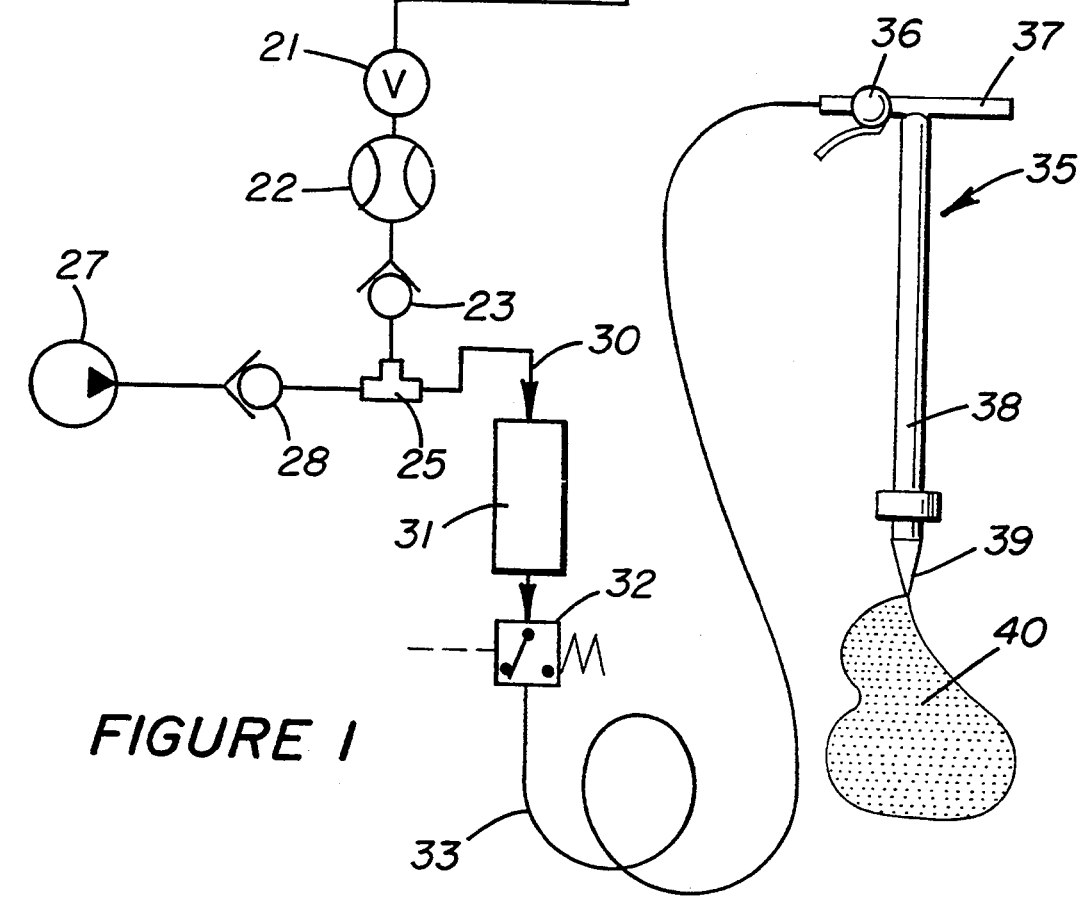
FIG. 1 is a partly diagrammatic view in elevation of the system embodying the principles of the invention.

As shown in FIG. 1, there may be a tank 10 containing liquid such as water containing a suitable pesticide and a suitable foam generating chemical, all at suitable concentrations. The tank 10 is connected by a conduit 11 to a pump 12. An engine (eng) 13 or motor is also connected to the pump 12 directly by a coupling 14. A pressure regulator 16 may be connected to the pump 12 and has a return for excess solution to the tank 10.

A flexible conduit 20 with the pressure gauge 15, which is of substantial length leads from the pump 12 to a ball valve 21. The liquid goes from the ball valve 21 to a flowmeter 22 and from there, via a check valve 23 to a siphon 25. There it is joined by a stream of air from a compressor (comp) 27 through a check valve 28. The resultant mix of air and liquid goes to a conduit or hose 30 and passes through a mixing chamber 31 (containing mixing beads or other static mixing devices to properly commingle the air and liquid for foam formation) and through a pressure sensor of a pressure sensitive switch 32 and into a long flexible conduit or hose 33 that goes to an applicator probe 35 via a trigger valve 36 in a probe handle 37. In the applicator probe 35, the foam passes through a pipe 38 with a rubber cone tip 39 for providing a seal against back flow around the holes (such as the hole 43) into which foam 40 is ejected.

The handle 37 of the applicator probe 35, which feeds the foam 40 to the application area, has a trigger type valve 36 to enable instantaneous stoppage of the foam flow when a desired amount of foamed substance has been ejected. The pressure-sensitive switch 32 on the hose 33 may be used to turn off the compressor 27 and thereby, if necessary prevent undue pressure in the hose 33 when the applicator trigger valve 36 is closed. When filling a confined space, monitor tubes (not shown) may be placed in the holes 41 and 42 on each side of the hole 43 (FIG. 4) through which the foam 40 is to be injected below a slab 44, to indicate when the foam substance has filled a cavity 45 to the monitored recess. The foam applicator probe 35 and tubes may then be moved to another hole and the process continued until all of the holes needed have been used to inject the foam 40.

As seen from this method, the invention provides, or can provide, a continuous "barrier" of the residual pesticide within the areas 45 that should be reached, and the foam can be confined in spaces; both conditions are impossible to achieve in ordinary ways with liquids or with dry foams. The invention reduces the amount of the pesticide needed to create this continuous barrier and to fill the cavities 45 and therefore, is economical and ecologically advantageous. The foaming of the pesticide reduces the loss of substance through volatilization or through exfiltration through porous bases or areas. Also the invention reduces the risk of ground and ground-water contamination by means of limiting the amount of pesticide which is applied, avoiding overdosing, and by means of the characteristics of the foam 40 itself. Effective kill and the residual nature of the pesticide render frequent retreatments unnecessary; retreatments can create an ecological disadvantage due to contamination at the building site or of ground water.

By reaching the pests at the location where they are most likely to be found, and also by attacking them at points where they tend to concentrate, economies are also inherent in the process. The foam 40 may collect in the cavity 45 until the cavity 45 is filled, if desired, or it can be used to fill only a desired portion of the cavity. By flowing upwardly and collecting, the foam 40 can contact the bottom 46 of a concrete slab 44 or other such structures and deposit the pesticidal material there in a location where ordinarily fumigant would be inconvenient to apply, and liquids almost impossible.

Figure 4:
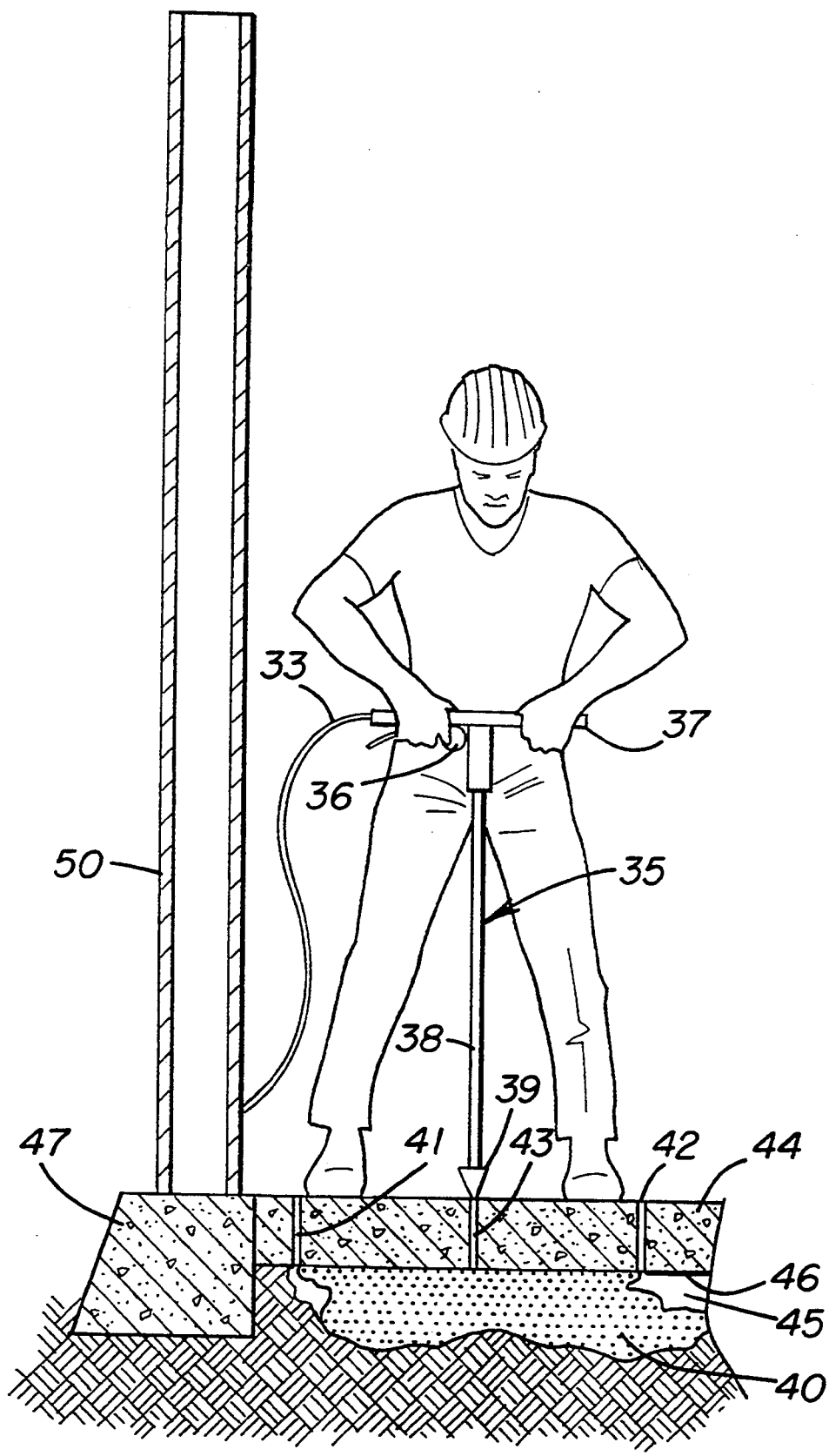
FIG. 4 is a similar view showing pesticidal foam applied through openings drilled through a slab, according to the method of the invention; the foam also travels out toward the center and sides of the slab, and can fill cavities which are formed by settling and by other changes in the ground relative to the slab, that occur after the construction and also cover the bottom of the slab.
Figure 5:
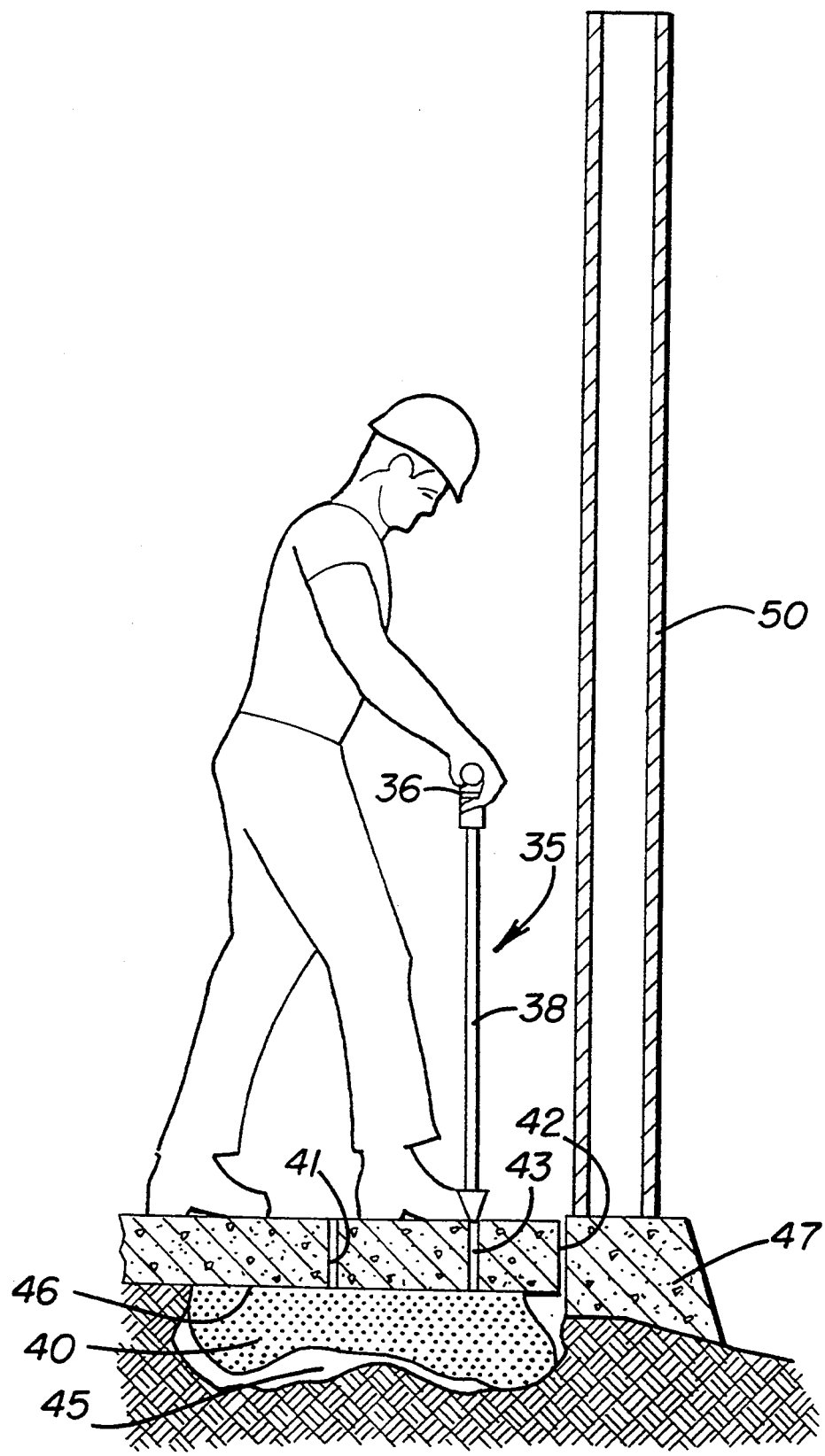
FIG. 5 is a similar view looking from another angle.

As the FIGS. 4 and 5 show, foam 40 is applied to a confined space 45, such as that beneath a concrete slab 44. The foam 40 application may be preceded by drilling or otherwise providing a series of holes 41, 42, 43 through the slab 44 along footings 47. Since the pests need to travel, in many instances, along the footings 47 or over the footings 47 in order to enter the building, pesticide can be transported by the foam 40 to treat the footings 47 and protect the building from the pests.

Figure 3:
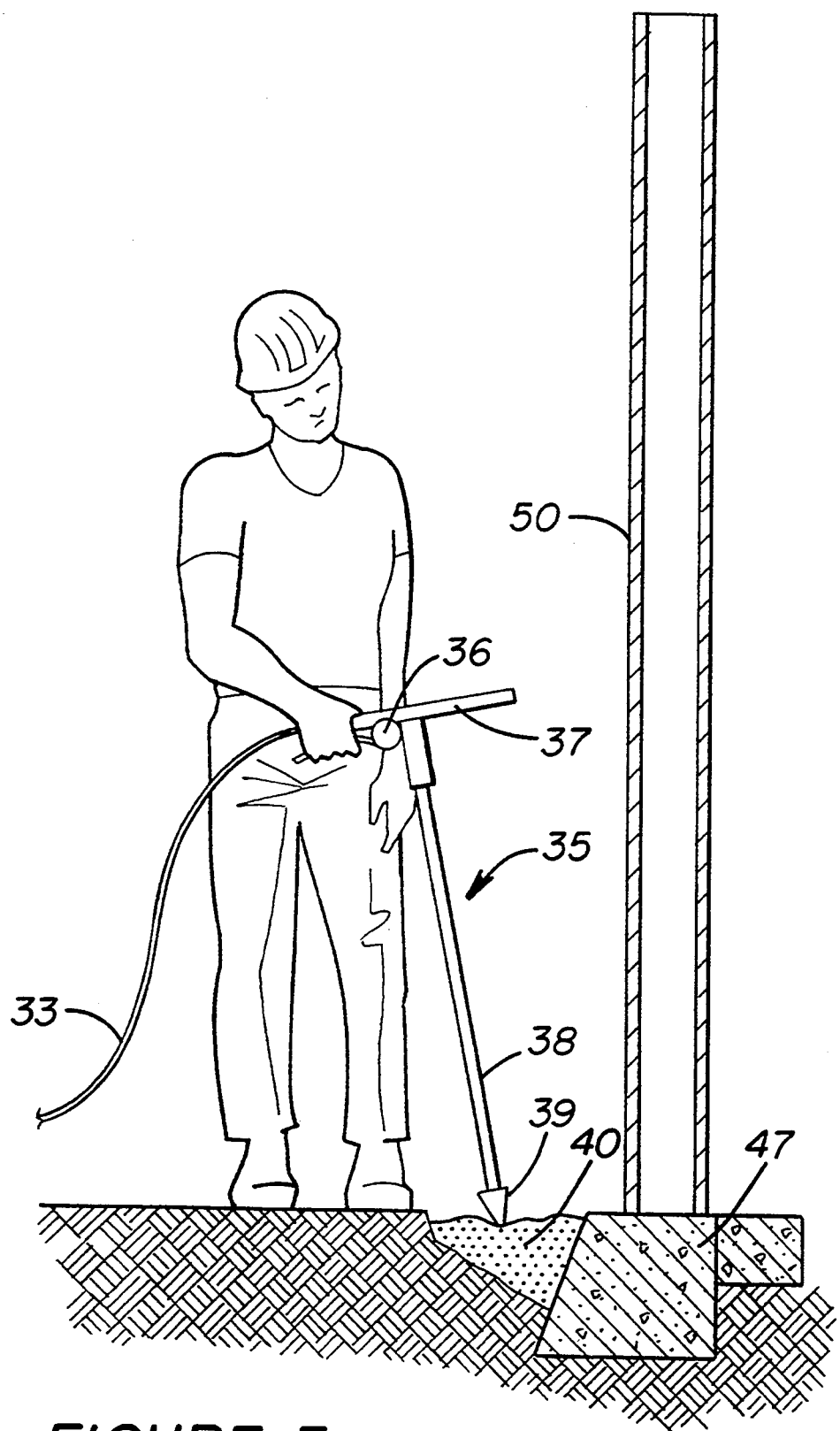
FIG. 3 is a diagrammatic view in elevation and partly in section of a man applying pesticide foam along a trench outside footings to cut off pests from entering the building from the outside.

Trenching treatments outside a building, or even all the way around it (FIG. 3), may be a very valuable way of reaching certain pests. The applicator probe 35 may be used with a trenching foot (not shown) on the end of the applicator probe 35 that can be used to help spread the foam evenly, while allowing it to build up to a height, thus assuring correct concentrations.

To those skilled in the art to which this invention relates, many changes in construction and widely differing embodiments and applications of the invention will suggest themselves without departing from the spirit and scope of the invention. The disclosures and the descriptions herein are purely illustrative and are not intended to be in sense limiting.

INDUSTRIAL APPLICABILITY

The invention provides a foam which includes a residual pesticide and which can effectively deposit such a pesticide beneath building slabs in such a manner that substantially full coverage of the ground beneath the slab can be attained even if the ground surface is very uneven and irregularly shaped. An effective amount of the pesticide can be deposited even in the relatively small space, often only a few inches high, beneath a building slab or floor and using a solution which contains only an allowable amount of pesticide since the foam used is a wet foam which has a relatively low expansion ratio. Such foams are particularly useful for applying termiticides.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

That which is claimed is:

1. A method of controlling pests selected from the group consisting of termites, ants, spiders, mites, roaches, fleas, house nesting flies, silverfish, lice, earwigs, wasps, bees, sowbugs and crickets, comprising the steps of:

mixing a liquid foamable residual pesticide with a foaming agent, water and air, the pesticide being selected from the group consisting of the carbamates, the pyrethrins, the pyrethroids, the organophosphates, the chlorinated hydrocarbons and the borates, to produce a temporary non-solidifying pesticidal wet foam having an expansion ratio, defined as the ratio of the final foam volume to the sum of the volumes of the pesticide, the foaming agent and the water, of between 20 to 1 and 5 to 1 and a flowability of less than about 30 seconds; and applying said foam, with repetition if necessary, at a locus whereby the foam contacts a surface which defines the locus, and thereafter deposits the pesticide on the surface and dissipates, so as to provide effective residual pesticidal activity on the surface.

2. A method as set forth in claim 1, wherein the locus is the space beneath a concrete slab.

3. A method as set forth in claim 2, wherein the foam dissipates in from about 5 minutes to about 20 minutes after it is formed.

4. A method as set forth in claim 1, wherein the foam dissipates in from about 5 minutes to about 20 minutes after it is formed.

5. A method as set forth in claim 1, wherein the expansion ratio is between 15 to 1 and 6 to 1.

6. A method as set forth in claim 5, wherein the expansion ratio is between 12 to 1 and 7 to 1.

7. A method as set forth in claim 5, wherein the foam has a flowability of less than about 20 seconds.

8. A method as set forth in claim 7, wherein the locus is the space beneath a concrete slab.

9. A method as set forth in claim 8, wherein the foam dissipates in from about 5 minutes to about 20 minutes after it is formed.

10. A method as set forth in claim 7, wherein the foam dissipates in from about 5 minutes to about 20 minutes after it is formed.

11. A method of controlling pests selected from the group consisting of termites, ants, spiders, mites, roaches, fleas, house nesting flies, silverfish, lice, earwigs, wasps, bees, sowbugs and crickets beneath a concrete-slab-based building or concrete slabs associated with other buildings, comprising the steps of:

forming holes through the slab along its marginal edges or other areas within the slab to a locus beneath the slab;

mixing a liquid foamable residual pesticide, the pesticide being selected from the group consisting of the carbamates, the pyrethrins, the pyrethroids, the organophosphates, the chlorinated hydrocarbons and the borates, with a foaming agent, water and air to produce a temporary non-solidifying pesticidal wet foam having an expansion ratio, defined as the ratio of the final foam volume to the sum of the volumes of the pesticide, the foaming agent and the water, of between 10 to 1 to 1 and a flowability of less than about 30 seconds; and injecting the pesticidal foam, with repetition if necessary, through the holes so that the injected foam contacts a surface which defines the locus and thereafter deposits the pesticide on the surface and dissipates, so as to provide effective residual pesticidal activity on the surface.

12. A method as set forth in claim 11, wherein the foam dissipates in from about 5 minutes to about 20 minutes after it is formed.

13. A method as set forth in claim 11, wherein the expansion ratio is between 15 to 1 and 6 to 1.

14. A method as set forth in claim 13, wherein the expansion ratio is between 12 to 1 and 7 to 1.

15. A method as set forth in claim 13, wherein the foam has a flowability of less than about 15 seconds.

16. A method as set forth in claim 15, wherein the foam dissipates in from about 5 minutes to about 20 minutes after it is formed.

17. A method as set forth in claim 11, wherein the foam dissipates in from about 5 minutes to about 20 minutes after it is formed.

18. A method as set forth in claim 5, wherein the expansion ratio is between 12 to 1 and 6 to 1.

19. A method as set forth in claim 13, wherein the expansion ratio is between 12 to 1 and 6 to 1.

* * * * *

UNITED STATES PATENT AND TRADEMARK OFFICE
CERTIFICATE OF CORRECTION

PATENT NO. : 5,346,699
DATED : September 13, 1994
INVENTOR(S) : BARBARA H. TIERNAN, et al.

It is certified that error appears in the above-indentified patent and that said Letters Patent is hereby corrected as shown below:

Column 10, line 27, after "of between" and before "and a flowability", delete [10 to 1 to 1] and insert --20 to 1 and 5 to 1--.

Signed and Sealed this

Twenty-seventh Day of August, 1996

*Attest:*

BRUCE LEHMAN

*Attesting Officer*     *Commissioner of Patents and Trademarks*

REEXAMINATION CERTIFICATE (3571st)

United States Patent [19]

Tiernan et al.

[11] B1 5,346,699

[45] Certificate Issued Jul. 14, 1998

[54] METHOD FOR CONTROLLING PESTS BY A PESTICIDE FOAM

[75] Inventors: Barbara H. Tiernan, Cupertino; Stanley M. Woogerd, San Rafael, both of Calif.

[73] Assignee: Foam Innovations, Inc., Pleasanton, Calif.

Reexamination Request:
No. 90/004,299, Jul. 8, 1996

Reexamination Certificate for:
Patent No.: 5,346,699
Issued: Sep. 13, 1994
Appl. No.: 63,361
Filed: May 17, 1993

Certificate of Correction issued Aug. 27, 1996.

Related U.S. Application Data

[63] Continuation of Ser. No. 739,139, Jul. 31, 1991, abandoned, which is a continuation-in-part of Ser. No. 648,142, Apr. 11, 1991, abandoned, which is a continuation of Ser. No. 346,644, May 3, 1989, abandoned.

[51] Int. Cl.$^6$ ........................................ A01N 25/16
[52] U.S. Cl. .................. 424/405; 424/43; 424/DIG. 11; 514/919; 514/945
[58] Field of Search .................. 424/43, 405, DIG. 11

[56] References Cited

U.S. PATENT DOCUMENTS 5,346,699  9/1994  Tiernan et al. ........................ 424/405

OTHER PUBLICATIONS

Foamite, Inc. Foamaster Termiticide Applicator Literature, Distributor 1981.

Pest Management; Jul. 1983 vol. 2 #7 Field Evaluation of Foamasil.

Pest Management Jul. 1983, vol. 2 #5 Field Evaluation of Pest–A–Foam.

Borg Industries, Ltd. Pestifoamer Model KT340 Undated Distributor Literature.

Response to Office Action of Hubert Dubb Dec. 13, 1993.

Pestifoamer Distributor Literature form 1818509, Date Stamped Sep. 1985, of Borg Industries.

*Primary Examiner*—Neil Levy

[57] ABSTRACT

A method is set forth of controlling pests such as termites. The method comprises mixing a residual pesticide with a foaming agent, water and air to produce a temporary non-solidifying pesticidal foam having an expansion ratio, defined as the ratio of the final foam volume to the sum of the volumes of the pesticide, the foaming agent and the water, of between 20 to 1 and 5 to 1. The foam is applied at a locus whereby it contacts a surface which defines the locus, and thereafter deposits the pesticide on the surface and dissipates, so as to provide residual pesticidal action on the surface.

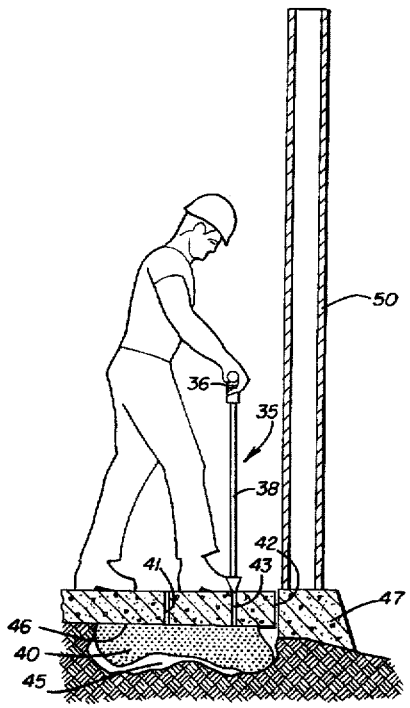

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–19 is confirmed.

* * * * *